United States Patent

Smith

(10) Patent No.: US 7,036,351 B2
(45) Date of Patent: May 2, 2006

(54) COMPENSATED OPEN-LOOP CONTROL OF OXYGEN SENSOR HEATER

(75) Inventor: James Craig Smith, Farmington Hills, MI (US)

(73) Assignee: Delphi Technologies, Inc., Troy, MI (US)

( * ) Notice: Subject to any disclaimer, the term of this patent is extended or adjusted under 35 U.S.C. 154(b) by 157 days.

(21) Appl. No.: 10/835,188

(22) Filed: Apr. 28, 2004

(65) Prior Publication Data

US 2005/0241361 A1    Nov. 3, 2005

(51) Int. Cl.
*G01N 27/12* (2006.01)

(52) U.S. Cl. ....................................... 73/23.2
(58) Field of Classification Search ................. 73/1.06, 73/23.2; 701/101, 105, 109
See application file for complete search history.

(56) References Cited

U.S. PATENT DOCUMENTS

| 5,001,643 A | * | 3/1991 | Domino et al. ............. 701/109 |
| 6,336,354 B1 | * | 1/2002 | Suzuki et al. .............. 73/31.05 |
| 6,742,379 B1 | * | 6/2004 | Matsubara et al. .......... 73/1.06 |

* cited by examiner

*Primary Examiner*—Robert Raevis
(74) *Attorney, Agent, or Firm*—Jimmy L. Funke

(57) ABSTRACT

An oxygen sensor heater control determines heater activation based on an open-loop control parameter and a correction factor that compensates for part-to-part variability. Following a cold start where the heater temperature can be reliably estimated, the engine controller predicts the resistance of the heating element and heater circuit at the desired operating temperature of the sensor, and computes the correction factor for heater activation based on the predicted resistance values and nominal resistance values. At least one predicted value is stored in non-volatile memory, and used to compute the correction factor following a warm or hot start of the engine.

8 Claims, 3 Drawing Sheets

COMPENSATED OPEN-LOOP CONTROL OF OXYGEN SENSOR HEATER

TECHNICAL FIELD

The present invention relates to the control of an exhaust gas oxygen sensor having an integral heater, and more particularly to a method of operating the heater that compensates for variations due to manufacturing tolerances.

BACKGROUND OF THE INVENTION

Exhaust gas oxygen sensors are sometimes equipped with an integral heating element that is electrically activated following engine starting to quickly bring the oxygen sensor to a desired operating temperature such as 700° C. This minimizes the interval of open-loop fuel control following a cold engine start, and maintains a predictable relationship between the oxygen sensor output signal and the exhaust gas equivalence or air/fuel ratio. In cases where the heating element is in close proximity to the oxygen sensor, the temperature of the oxygen sensor can be inferred from the resistance of the heating element. However, the heater includes conductor leads in addition to the heating element, and the resistance of the conductor leads can vary significantly due to part-to-part variability and variations in operating temperature. As a result, it can be difficult to reliably maintain the oxygen sensor at the desired operating temperature.

SUMMARY OF THE INVENTION

The present invention is directed to an improved method of operation for an oxygen sensor heater circuit including an electrical heating element and conductor leads, where heater activation is determined based on an open-loop control parameter that accounts for external heating of the sensor and a correction factor that compensates for sensor variability. Following a cold start where the heater circuit temperature can be reliably established, the engine controller predicts the resistance of the heating element and heater circuit at the desired operating temperature of the sensor, and computes the correction factor for heater activation based on the predicted resistance values and nominal resistance values. The predicted resistance of the heating element is stored in non-volatile memory, and used to compute the correction factor following a warm or hot start of the engine.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
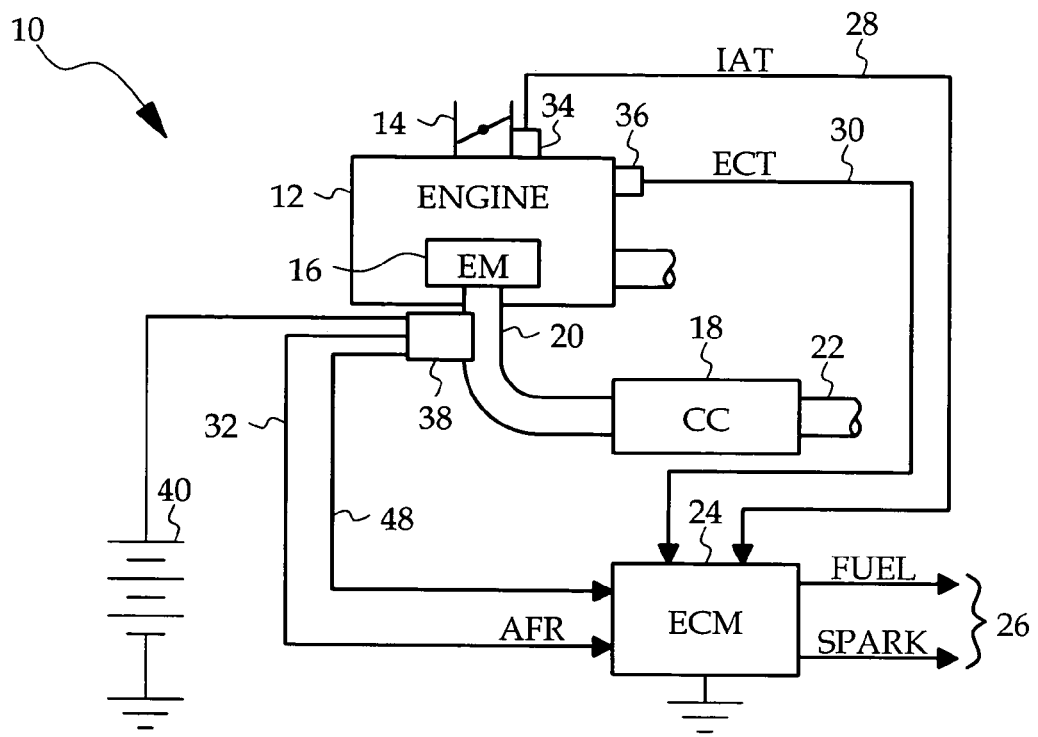
FIG. 1 is a diagram of a motor vehicle engine including an exhaust gas oxygen sensor with integral heater and a microprocessor-based engine control module (ECM) for controlling activation of the oxygen sensor heater in accordance with this invention.

Referring to the drawings, and particularly to FIG. 1, the reference numeral 10 generally designates a motor vehicle powerplant including a spark ignition internal combustion engine 12. Engine 12 receives intake air through a throttled intake manifold 14, burns a metered mixture of air and fuel, and releases the exhaust gasses into exhaust manifold (EM) 16. The exhaust gases are coupled to a catalytic converter (CC) 18 via one or more header pipes 20, and then to a tailpipe 22. A microprocessor-based engine control module (ECM) 24 regulates fuel injection and spark timing control functions for engine 10 as indicated by the reference numeral 26. These and other control functions are carried out based on driver demand and various measured engine operating parameters, including the inlet air temperature IAT on line 28, the engine coolant temperature ECT on line 30 and the exhaust gas air/fuel ratio AFR on line 32. The IAT and ECT parameters are measured by conventional temperature sensors 34 and 36, respectively, and the AFR parameter is measured by an engine exhaust gas oxygen sensor 38 having a zirconia sensing element positioned in the exhaust gas stream in header 20. The oxygen sensor 38 also includes an integral electrical resistance heating element (designated in FIG. 2 by the reference numeral 38a) that is activated by ECM 24 following starting of engine 10 to quickly bring the zirconia sensing element to a desired operating temperature such as 700° C. This allows faster initiation of closed-loop fuel control by ECM 24 following a cold engine start, and maintains a consistent and desired relationship between the oxygen sensor output signal on line 32 and the exhaust gas equivalence or air/fuel ratio.

The oxygen sensor 38 is preferably a planar device such as the INTELLEK OSP sensor manufactured and sold by Delphi Corporation, in which the zirconia sensing element, the heating element, and the associated conductor leads are manufactured by depositing and firing specially formulated thick film inks on ceramic substrates. For a detailed description of the INTELLEK OSP sensor, see SAE Paper No. 2000-01-088, authored by Yoo, Bonadies, Detwiler, Ober and Reed, and presented in 2000.

Figure 2:
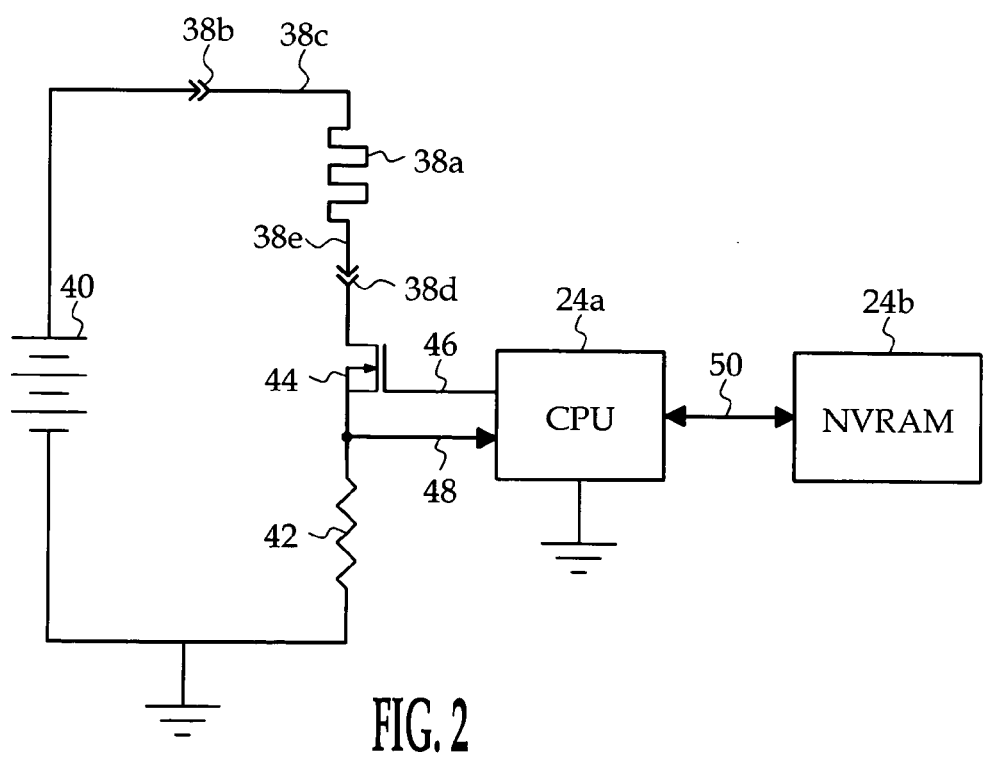
FIG. 2 is a diagram of a circuit for activating the oxygen sensor heater of FIG. 1.

Electrical current for activating the heating element 38a of oxygen sensor 38 is provided by the vehicle storage battery 40. As illustrated in FIG. 2, the positive terminal of battery 40 is coupled to one end of heating element 38a via connector terminal pair 38b and conductor lead 38c, and the negative terminal of battery 40 is coupled to the other end of heating element 38a via sense resistor 42, MOSFET 44, connector terminal pair 38d and conductor lead 38e. As indicated in FIG. 1, sense resistor 42 and MOSFET 44 are preferably integrated into ECM 24. Referring to FIG. 2, ECM 24 additionally includes a central processing unit CPU 24a and a non-volatile memory NVRAM 24b. The CPU 24a modulates the conduction of MOSFET 44 via line 46, and samples the voltage across sense resistor 42 via line 48 to determine the heating element current. The non-volatile memory 24b is coupled to CPU 24a by a data bus 50, and stores one or more learned parameters for computing a correction factor CF that adjusts the modulation of MOSFET 44 according to this invention.

As mentioned above, ECM 24 will ideally regulate the current supplied to oxygen sensor heating element 38a to quickly heat the zirconia sensing element to a desired operating temperature such as 700° C., and to thereafter maintain it substantially at that temperature. While it can be reliably assumed that the temperatures of the sensing element and the heating element 38a are virtually the same due to close thermal coupling, that temperature must be estimated based on measured and known parameters, including the terminal voltage of battery 40, the heating element current, the heating element's thermal coefficient of resistance, the on-resistance of MOSFET 44, the harness and connector resistances, and the resistance of sense resistor 42. In effect, the voltage, current and resistance parameters are used to determine the overall resistance of the oxygen sensor heater circuit (that is, the heater element 38a and the conductor leads 38c and 38e), and the thermal coefficient of resistance is used to convert the overall resistance to a corresponding temperature. Unfortunately, estimation errors occur because the overall resistance includes the resistance of the thick film conductor leads 38c, 38e, and the resistance of the thick film conductor leads 38c, 38e is subject to variation due to manufacturing tolerances and operating temperature. Manufacturing tolerances stem from variations in the width and thickness of the conductor leads, and temperature effects stem from conductive and convective heating of the conductor leads 38c, 38e by the exhaust header 20 and the exhaust gasses flowing therethrough. These lead resistance variations produce a corresponding variation in the overall resistance of the heater circuit that is not related to the temperature of the heating element 38a, thereby introducing error in the estimated heating element temperature. The heating effects can be addressed by estimating the rate of heat transfer to the oxygen sensor 38, but variations due to manufacturing tolerances remain un-addressed.

The method of the present invention overcomes the above-described difficulties with a control including an open-loop regulation of heater activation that accounts for external heating of the oxygen sensor and an activation correction factor CF that compensates for variability due to manufacturing tolerances. Briefly, the correction factor CF is determined following a cold start where the temperature of the heating element 38a can be reliably estimated based on IAT and/or ECT. Under these conditions, ECM 24 can predict what the resistances of heating element 38a and the overall heater circuit (i.e., the heating element and the conductor leads 38c and 38e) will be when the zirconia element reaches its desired operating temperature. The correction factor CF is then calculated based on ratios of the predicted resistance values and nominal resistance values. The predicted resistance of the heating element is stored in non-volatile memory 24b and used to compute the correction factor CF following a warm or hot start of engine 10.

Figure 3:
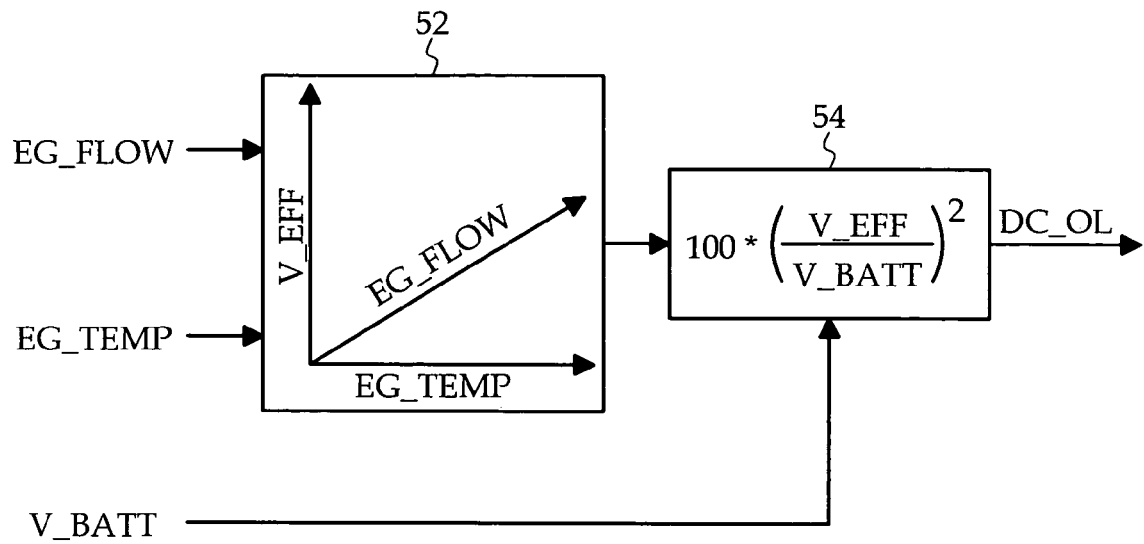
FIG. 3 is a block diagram depicting an open-loop table look-up method implemented by the ECM of FIG. 1 for scheduling oxygen sensor heater activation based on estimated exhaust gas parameters.

Referring to FIG. 3, the open-loop control can be implemented by calibrating a look-up table of heater voltage values (effective voltage V_EFF) as a function of estimated exhaust gas temperature and flow parameters EG_TEMP, EG_FLOW, and converting the V_EFF table output to a corresponding PWM duty cycle DC for MOSFET 44 based on the actual driving voltage at the terminal pair 38b (referred to herein as the battery voltage V_BATT). The exhaust gas parameters EG_TEMP and EG_FLOW may be measured, or more likely, estimated based on other more commonly measured parameters such as mass air flow, engine speed, air/fuel ratio, and so on. A representative technique for estimating exhaust gas parameters is described, for example, in SAE Paper No. 980517, authored by Maloney and Olin, and presented in 1997. Referring to FIG. 3, the block 52 designates the look-up table, while the block 54 designates the conversion of effective voltage V_EFF to a corresponding open-loop PWM duty cycle DC_OL.

Figure 4:
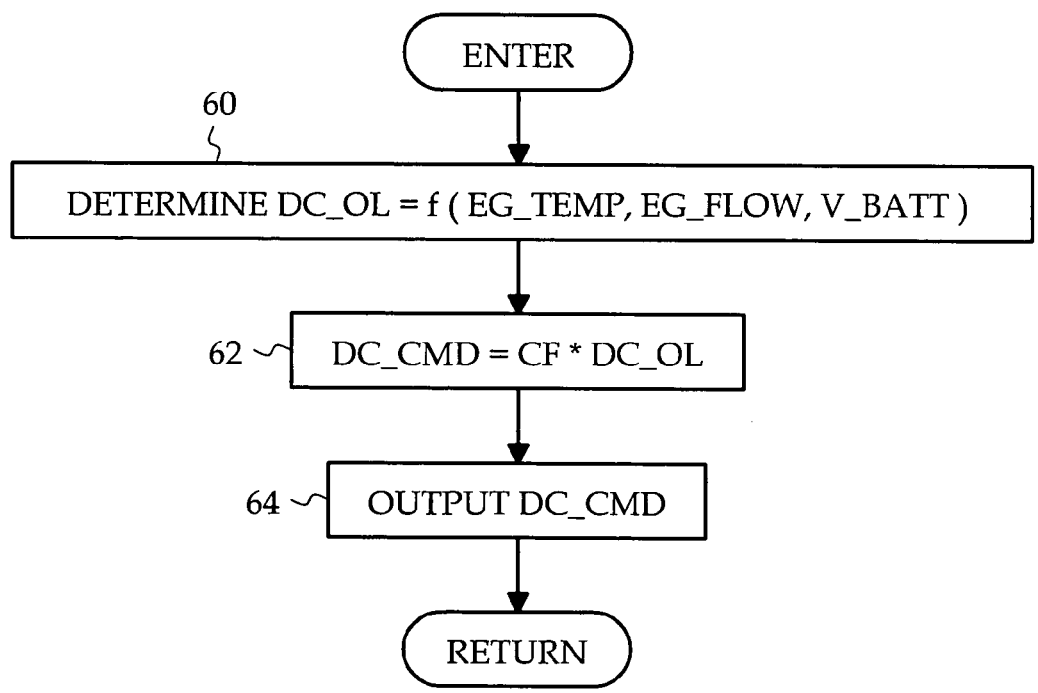
FIG. 4 is a flow diagram illustrating a routine carried out by the ECM of FIG. 1 for activating the oxygen sensor heater based on an open-loop duty-cycle term and a learned correction factor.
Figure 5:
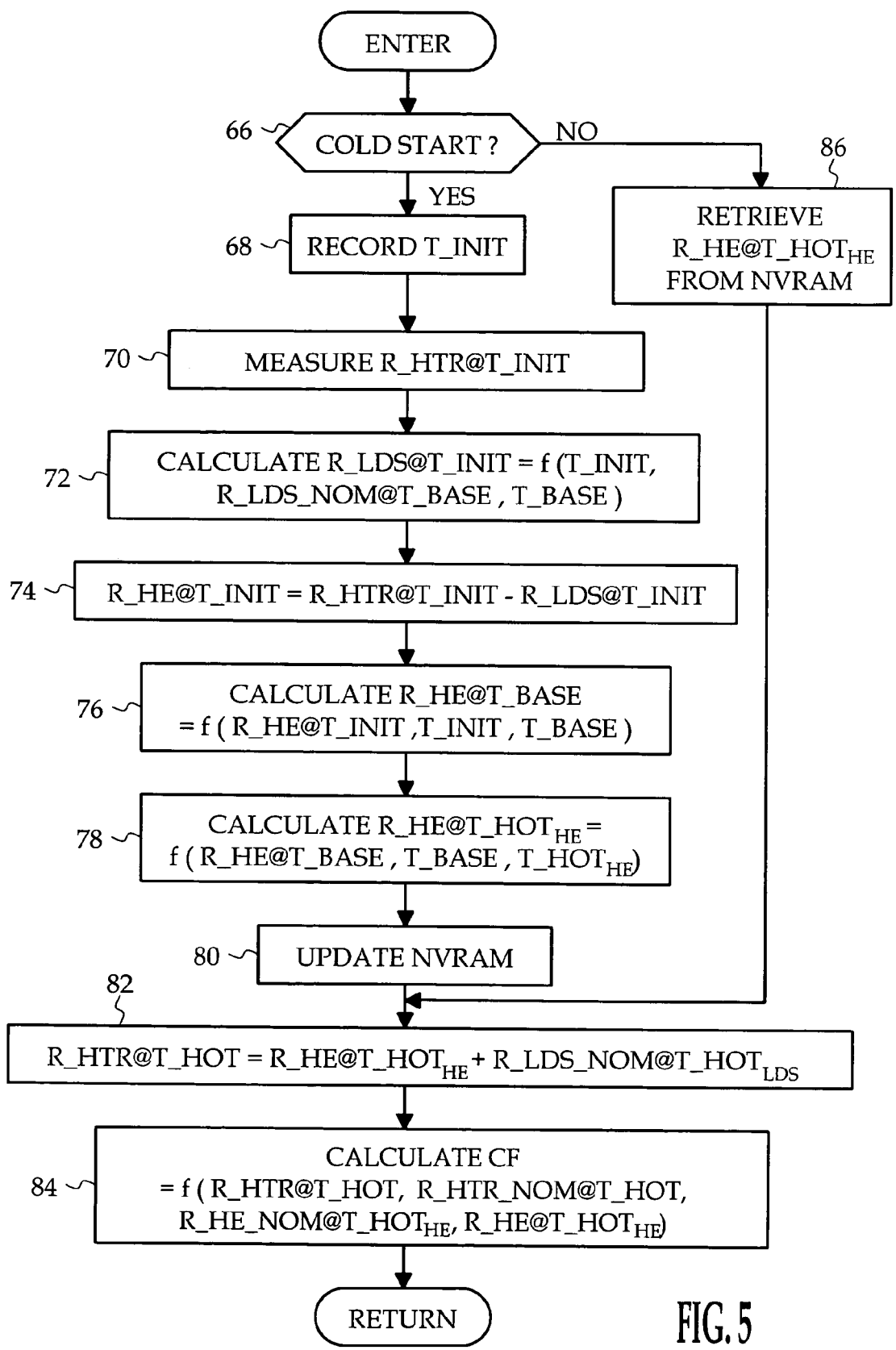
FIG. 5 is a flow diagram illustrating a routine carried out by the ECM of FIG. 1 for updating the correction factor used in the routine of FIG. 4.

The flow diagrams of FIGS. 4 and 5 represent software routines that are executed by the CPU 24a of ECM 24 in carrying out the method of this invention. FIG. 4 depicts a high level routine that is periodically executed during engine operation for developing an open-loop duty cycle DC_OL for MOSFET 44 based on exhaust gas parameters EG_TEMP and EG_FLOW, battery voltage V_BATT, and correction factor CF. FIG. 5 depicts a routine that is executed at engine key-on for initializing or updating the correction factor CF.

Referring to FIG. 4, the block 60 determines the open-loop duty cycle DC_OL as a function of EG_TEMP, EG_FLOW and V_BATT. As indicated above in reference to FIG. 3, the effective voltage V_EFF may be determined by table-look-up based on exhaust gas parameters such as EG_TEMP and EG_FLOW. The table data is calibrated based on measured characteristics of a nominal oxygen sensor 38, and may be based on alternate or additional parameters, depending on the nature of the available data. In any event, however, the effective voltage V_EFF is calibrated to produce optimal activation of the heating element 38a with the nominal sensor 38. The block 62 applies the correction factor CF to DC_OL to form a duty-cycle command DC_CMD, and the block 64 outputs an activation signal to MOSFET 44 based on DC_CMD.

Referring to FIG. 5, the block 66 is first executed to determine if specified cold start conditions are in effect. For example, a cold start may be detected if IAT and/or ECT are essentially equivalent, and the engine 12 has been inoperative for at least a predefined time period such as two hours. If the cold start conditions are met, the block 68 records an initial temperature T_INIT based on IAT or ECT, the assumption being that the initial temperature also holds true for the various components of oxygen sensor 38. Then the block 70 is executed to measure the initial overall heater resistance R_HTR@T_INIT—that is, the combined resistance of heater element 38a and conductor leads 38c and 38e. As indicated above, the overall heater resistance is computed based on the battery voltage V_BATT (i.e., the driving voltage at the terminal pair 38a), the measured heater current, the heater's thermal coefficient of resistance, the on-resistance of MOSFET 44, the harness and connector resistances, and the resistance of sense resistor 42. Given T_INIT, R_HTR_INIT and a nominal resistance R_LDS_NOM@T_BASE of the conductor leads 38c and 38e at a specified base temperature T_BASE (which may be 22° C., for example), the block 72 calculates the resistance R_LDS@T_INIT of the conductor leads 38c, 38e at initial temperature T_INIT, based on the equation:

$$R\_LDS@T\_INIT = R\_LDS\_NOM@T\_BASE \cdot [1 + \alpha \cdot (T\_INIT - T\_BASE)]$$

where α is the thermal coefficient of resistance of the material used to form conductor leads 38c and 38e. The block 74 then subtracts R_LDS@T_INIT from the measured initial overall heater resistance R_HTR@T_INIT to find the resistance R_HE@T_INIT of the heating element 38a at the initial temperature T_INIT. Given T_INIT, T_BASE and R_HE@T_INIT, the block 76 then calculates the resistance R_HE@T_BASE of the heating element 38a at base temperature T_BASE using the equation:

$$R\_HE@T\_BASE = (M \cdot R\_HE@T\_INIT)/(T\_INIT + M - T\_BASE)$$

where M is the reciprocal of the thermal coefficient of resistance α. Finally, the block 78 calculates the resistance $R\_HE@T\_HOT_{HE}$ of the heating element 38a at its hot operating temperature $T\_HOT_{HE}$ (which may be 700° C., for example) using the equation:

$$R\_HE@T\_HOT_{HE}=R\_HE@T\_BASE \cdot [1+\alpha \cdot (T\_HOT_{HE}-T\_BASE)]$$

The block 80 updates non-volatile memory 24b with the newly computed value of $R\_HE@T\_HOT_{HE}$. Initially, only a nominal value of $R\_HE@T\_HOT_{HE}$ is stored in memory 24b, and the CPU 24a simply over-writes with the value computed at the block 78. In subsequent executions of the routine, a first-order filter function may be used to update the stored value of $R\_HE@T\_HOT_{HE}$ based on a calibrated percentage of the difference between the new and stored values of $R\_HE@T\_HOT_{HE}$. If the cold start conditions are not met during such subsequent executions, the block 86 is executed to retrieve the stored value of $R\_HE@T\_HOT_{HE}$ from memory 24b, and the blocks 68–80 are skipped as indicated by the flow diagram lines.

Once the value of $R\_HE@T\_HOT_{HE}$ is obtained, the block 82 computes the overall resistance $R\_HTR@T\_HOT$ of the hot operational heater circuit according to the sum of $R\_HE@T\_HOT_{HE}$ and $R\_LDS\_NOM@T\_HOT_{LDS}$, where $R\_LDS\_NOM@T\_HOT_{LDS}$ is a nominal resistance of the conductor leads 38c and 38e at their nominal hot operating temperature $T\_HOT_{LDS}$ (which may be 400° C., for example). Finally, the block 84 calculates the correction factor CF as a function of $R\_HTR@T\_HOT$, $R\_HTR\_NOM@T\_HOT$, $R\_HE@T\_HOT_{HE}$, and $R\_HE\_NOM@T\_HOT_{HE}$, according to the expression:

$$\left(\frac{R\_HTR @ T\_HOT}{R\_HTR\_NOM @ T\_HOT}\right)^2 \cdot \left(\frac{R\_HE\_NOM @ T\_HOT_{HE}}{R\_HE @ T\_HOT_{HE}}\right)$$

The above expression for the correction factor CF can be derived by: (1) expressing the electrical heating (i.e., the RMS power) that will be achieved using a properly calibrated open-loop duty cycle (DC_OL) based on V_BATT and the nominal resistance values $R\_HTR\_NOM@T\_HOT$ and $R\_HE\_NOM@T\_HOT_{HE}$; (2) expressing the electrical heating that is achieved using an actual duty cycle (DC_CMD) based on V_BATT and the actual resistance values $R\_HTR@T\_HOT$ and $R\_HE@T\_HOT_{HE}$; and (3) equating the two expressions, yielding:

$$DC\_OL \cdot \left(\frac{V\_BATT}{R\_HTR\_NOM @ T\_HOT}\right)^2 \cdot R\_HE\_NOM @ T\_HOT_{HE} \equiv$$

$$DC\_CMD \cdot \left(\frac{V\_BATT}{R\_HTR @ T\_HOT}\right)^2 \cdot R\_HE @ T\_HOT_{HE}$$

Solving for DC-CMD yields the equation:

$$DC\_CMD =$$
$$DC\_OL \cdot \left(\frac{R\_HTR @ T\_HOT}{R\_HTR\_NOM @ T\_HOT}\right)^2 \cdot \left(\frac{R\_HE\_NOM @ T\_HOT_{HE}}{R\_HE @ T\_HOT_{HE}}\right)$$

which will be recognized as the equation carried out at the block 62 of FIG. 4.

The nominal resistance values used in the equations presented herein are based on resistance values specified by the oxygen sensor manufacturer. Given the nominal conductor lead and heating circuit resistances at base temperature T_BASE (that is, $R\_LDS\_NOM@T\_BASE$ and $R\_HTR\_NOM@T\_BASE$), the nominal resistance of the heating element 38a at base temperature T_BASE (that is, $R\_HE\_NOM@T\_BASE$) is determined according to the difference of $R\_HTR\_NOM@T\_BASE$ and $R\_LDS\_NOM@T\_BASE$. Then, given $R\_LDS\_NOM@T\_BASE$ and $R\_HE\_NOM@T\_BASE$, the nominal conductor leads and heating element resistances at the respective hot operating temperatures $T\_HOT_{LDS}$ and $T\_HOT_{HE}$ can be simply calculated as follows:

$$R\_LDS\_NOM@T\_HOT_{LDS}=R\_LDS\_NOM@T\_BASE\cdot[1+\alpha\cdot(T\_HOT_{LDS}-T\_BASE)]$$

and $$R\_HE\_NOM@T\_HOT_{HE}=R\_HE\_NOM@T\_BASE\cdot[1+\alpha\cdot(T\_HOT_{HE}-T\_BASE)]$$

And of course, $R\_HTR\_NOM@T\_HOT$ is simply the sum of $R\_HE\_NOM@T\_HOT_{HE}$ and $R\_LDS\_NOM@T\_HOT_{LDS}$.

In summary, the present invention provides a convenient and easily implemented method of optimally activating the heating element of an exhaust gas oxygen sensor with a calibrated open-loop control that is compensated for variations in heater lead resistance due to manufacturing tolerances. The method requires the sensor manufacturer to specify the nominal resistances of the heating element and its conductor leads at a base temperature. The hot operating resistances of the heating element and heating circuit are then predicted based on assumed hot operating temperatures of the heating element and its conductor leads, and the predicted and nominal resistances are used to compute a correction factor that adjusts the open-loop control to compensate for the conductor lead resistance variations.

While the method of the present invention has been described in reference to the illustrated embodiment, it will be recognized that various modifications in addition to those mentioned above will occur to those skilled in the art. For example, the base and operating temperatures may be different than mentioned herein, the correction factor CF may be stored in memory 24b, the powerplant 10 may include more than one oxygen sensor, and so on. Accordingly, it will be understood that methods incorporating these and other modifications may fall within the scope of this invention, which is defined by the appended claims.

The invention claimed is:

1. A method of operating an exhaust gas oxygen sensor for an engine, the oxygen sensor having a electrical heating circuit including a heating element and conductor leads attached to said heating element, where a temperature of the oxygen sensor is inferred from an electrical resistance of said heating element, the method comprising the steps of:
   electrically activating said heating circuit at an activation value determined in relation to external heat transfer to said oxygen sensor;
   determining an initial temperature of said heating circuit based on an initial cold start temperature of said engine;
   measuring an electrical resistance of said heating circuit at said initial temperature;
   predicting hot operational electrical resistances of said heating element and said heating circuit based on said measured resistance, assumed hot operational temperatures of said heating element and said conductor leads, and a nominal resistance of said conductor leads; and modifying said activation value based on said predicted hot operational electrical resistances, the nominal resistance of said conductor leads, the nominal resistance of said conductor leads, and a nominal resistance of said heater circuit so as to compensate for oxygen sensor variations.

2. The method of claim 1, including the steps of:

storing a computed parameter used to modify said activation value; and thereafter using the stored parameter to modify said activation value.

3. The method of claim 2, including the steps of:

repeating the method following a subsequent cold start of said engine to re-predict the hot operational electrical resistances of said heating element and said heating circuit; and updating said stored parameter based on the re-predicted hot operational electrical resistances.

4. The method of claim 1, where the nominal resistance of said conductor leads is specified for a base temperature, and the method includes the steps of:

determining a nominal resistance of said conductor leads for said initial temperature based on the specified nominal resistance of said conductor leads, said base temperature and said initial temperature;

determining a resistance of said heating element for said initial temperature according to a difference between the measured resistance of said heating circuit and said nominal resistance of said conductor leads for said initial temperature; and predicting the hot operational resistance of said heating element based on said resistance of said heating element for said initial temperature and the assumed hot operational temperature of said heating element.

5. The method of claim 4, including the steps of:

determining a nominal resistance of said conductor leads for said hot operational temperature of said conductor leads based on the specified nominal resistance of said conductor leads, said base temperature and said hot operational temperature of said conductor leads; and predicting the hot operational resistance of said heating circuit according to a sum of the predicted hot operational resistance of said heating element and said nominal resistance of said conductor leads for said hot operational temperature of said conductor leads.

6. The method of claim 1, including the steps of:

computing a correction factor for said activation value that will compensate said activation value for said oxygen sensor variations, based on said predicted hot operational electrical resistances, a nominal resistance of said heating element at said hot operational temperature of said heating element, and a nominal hot operational resistance of said heater circuit; and modifying said activation value by applying said correction factor to said activation value, and activating said heating element at the modified activation value.

7. The method of claim 6, where the nominal resistances of said heater circuit and said conductor leads are specified for a base temperature, and the method includes the steps of:

determining a nominal resistance of said heating element for said base temperature according to a difference between the specified nominal resistances of said heating circuit and said conductor leads;

determining the nominal resistance of said heating element for said hot operational temperature of said heating element based on said nominal resistance of said heating element for said base temperature, said base temperature, and said hot operational temperature of said heating element.

8. The method of claim 7, including the steps of:

determining a nominal resistance of said conductor leads for said hot operational temperature of said conductor leads based on the specified nominal resistance of said conductor leads, said base temperature and said hot operational temperature of said conductor leads; and determining a nominal hot operational resistance of said heater circuit according to a sum of said nominal resistance of said heating element for said hot operational temperature of said heating element and said nominal resistance of said conductor leads for said hot operational temperature of said conductor leads.

* * * * *